United States Patent [19]

Truelock

[11] 4,361,491
[45] Nov. 30, 1982

[54] SUPERCOOLED FLUIDS AND METHODS OF PRODUCING SUCH SUPERCOOLED FLUIDS

[75] Inventor: Donald E. Truelock, Moberly, Mo.

[73] Assignee: Kay Laboratories, Inc., San Diego, Calif.

[21] Appl. No.: 264,865

[22] Filed: May 18, 1981

Related U.S. Application Data

[63] Continuation of Ser. No. 945,871, Sep. 26, 1978, abandoned, which is a continuation-in-part of Ser. No. 847,141, Oct. 31, 1977, abandoned.

[51] Int. Cl.³ .............................. C09K 5/06; F24J 3/04
[52] U.S. Cl. .................................... 252/70; 23/302 R; 23/302 T; 126/263; 423/265; 423/266; 423/275; 423/514
[58] Field of Search ................... 252/70; 126/263, 400; 423/514, 265, 266, 275; 23/302 R, 302 T

[56] References Cited

U.S. PATENT DOCUMENTS

| | | | |
|---|---|---|---|
| 1,384,747 | 7/1921 | Eckelmann | 126/263 |
| 1,385,074 | 7/1921 | Ferguson | 126/263 |
| 1,570,047 | 1/1926 | Darrin | 23/302 R |
| 2,220,777 | 11/1940 | Othner | 126/263 |
| 2,289,425 | 7/1942 | Hogan | 126/263 |
| 2,827,438 | 3/1958 | Broadley | 252/70 |
| 3,093,308 | 6/1963 | Snelling | 126/263 |
| 3,951,127 | 4/1976 | Watson et al. | 252/70 X |
| 4,077,390 | 3/1978 | Stanley | 126/263 |
| 4,091,883 | 5/1978 | Schroder | 126/400 |

FOREIGN PATENT DOCUMENTS

| | | | |
|---|---|---|---|
| 2448739 | 9/1976 | Fed. Rep. of Germany | 252/70 |
| 50-90584 | 7/1975 | Japan | 252/70 |

*Primary Examiner*—Dennis L. Albrecht
*Attorney, Agent, or Firm*—Ellsworth R. Roston; Charles H. Schwartz

[57] ABSTRACT

This invention relates to a method of producing articles which generate heat at a substantially constant temperature for an extended period of time and which are able to remain in a stable state until such time as the generation of heat is desired. The method also relates to supercooled fluids produced by such methods. The method involves the processing of supercooled fluids such as hypo to produce this stable state. As a first step, a suitable material such as ethylene glycol may be added to the supercooled fluid to stabilize the supercooled fluid and to decrease the generation of heat in the supercooled fluid to obtain a desired temperature. The mixture is then heated to a relatively high temperature considerably above the melting temperature of the supercooled fluid. With the mixture at the high temperature, water is added to provide a particular specific gravity and an alkali is added to provide a particular pH.

The mixture may then be poured into rupturable pouches while being maintained at the high temperature. The mixture in the pouches is then allowed to cool slowly to ambient temperatures and is placed in a separate container with a triggering material.

12 Claims, 3 Drawing Figures

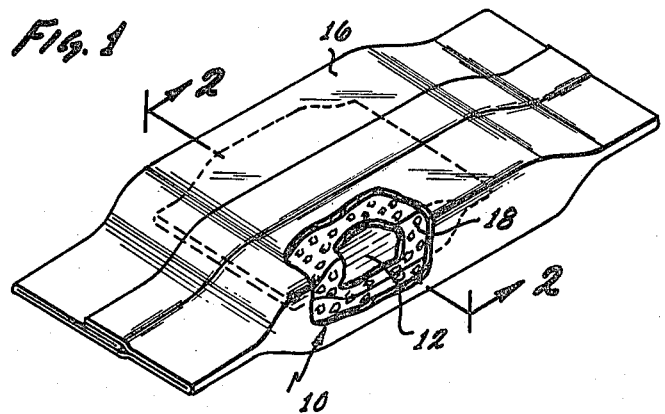
Fig. 1
Fig. 2
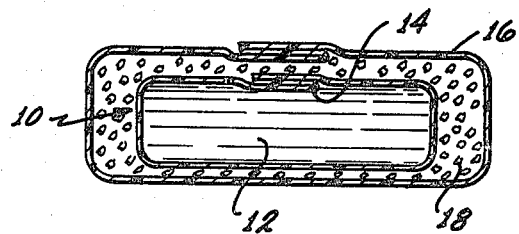
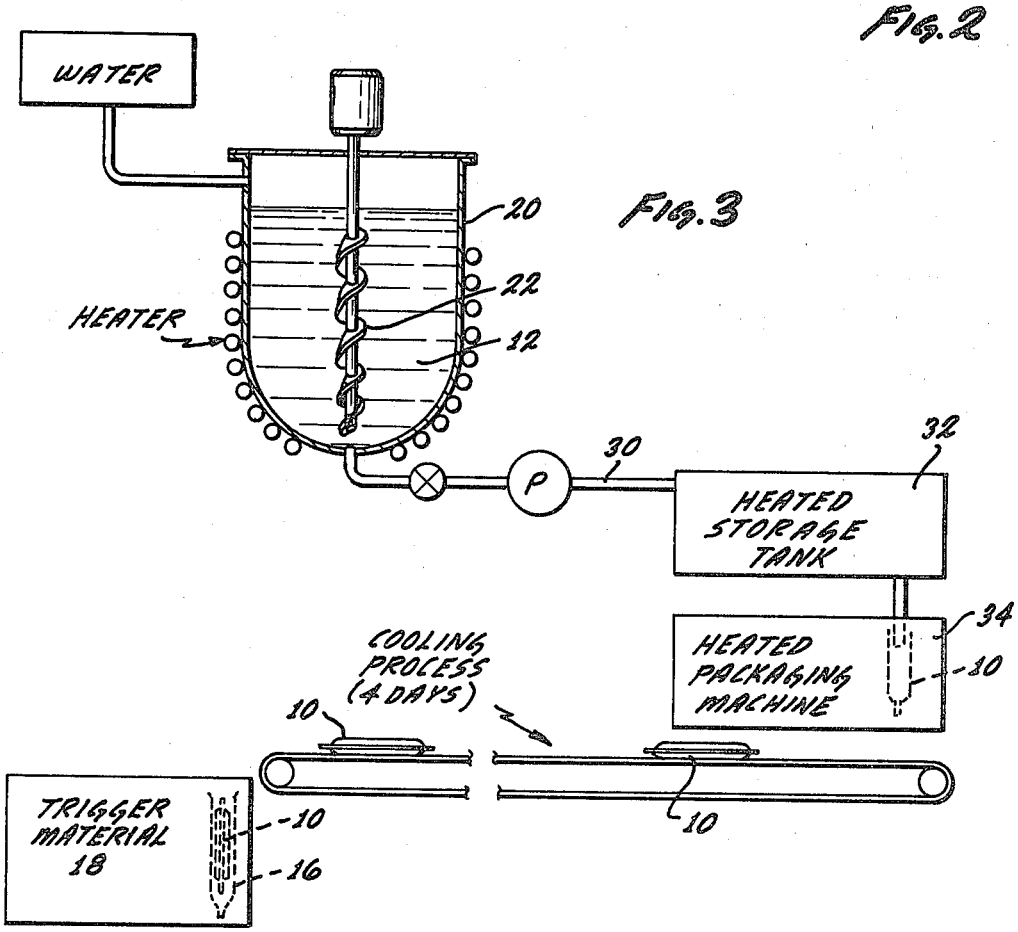
Fig. 3

SUPERCOOLED FLUIDS AND METHODS OF PRODUCING SUCH SUPERCOOLED FLUIDS

This is a continuation of application Ser. No. 945,871 filed Sept. 26, 1978 (now abandoned), which is in turn a continuation-in-part of application Ser. No. 847,141 filed Oct. 31, 1977 (now abandoned).

The invention relates to a method of processing supercooled fluids before the supercooled fluids are packaged. The invention particularly relates to methods of processing supercooled fluids to assure that the fluids will be retained in a fluid state until such time as it is desired to generate heat from the supercooled fluid. The invention further relates to a method of processing supercooled fluids to assure that the generation of heat from the supercooled fluid will occur at a particular temperature. The method also relates to supercooled fluids produced by such methods.

There are many different instances where it is desirable to generate heat for an extended period of time at a substantially constant temperature. For example, it is desirable to generate heat at a particular temperature for an extended period of time when babies are to be bathed or otherwise administered to in a hospital. It is further desirable to generate heat at a particular temperature at the heel of a baby in order to facilitate the withdrawal of blood from the vein or artery of a baby for purposes of testing the physical well-being of the baby.

Various attempts have been made in the past to generate heat at a predetermined and substantially constant temperature for an extended period of time. Until recently, it has been difficult to provide such a generation of heat. For example, chemicals have been mixed to produce an exothermic chemical reaction but the heat generated has peaked quickly at a relatively high value above the temperature desired and has then decreased progressively to a temperature below that desired. When the temperature of the chemical reaction is above that desired, the patient can become burned or produce other detrimental effects. When the temperature of the chemical reaction is below that desired, the patient does not receive beneficial results of an optimal nature.

Supercooled fluids have been known for some time to generate heat at a substantially constant temperature. The supercooled fluids melt from a solid state to a liquid state at a particular temperature and then become triggered from the liquid state to a solid crystalline state at the particular temperature. During the time the supercooled fluid becomes triggered to the crystalline state, it generates heat.

Although the desirable characteristics of supercooled fluids have been known for some time, supercooled fluids have had limited use. This has resulted from certain disadvantages in the supercooled fluid. For example, although supercooled fluids theoretically generate heat at a substantially constant temperature, the temperature cannot always be pre-established with great accuracy. As an illustration, under some conditions, a supercooled fluid will generate heat at a temperature of 118° F. and at other times the supercooled fluid will generate heat at a temperature of approximately 120° F. When a precise temperature is to be provided such as for medicinal purposes, such variations in temperature can cause great concern and be somewhat detrimental to the well-being of a patient.

There are other disadvantages to the use of supercooled fluid. Supercooled fluids tend to be somewhat unstable, particularly when subjected to relatively low temperatures. For example, when supercooled fluids tend to be subjected to temperatures below the freezing point of water, they tend to become automatically triggered from the fluid state to the solid crystalline state.

This invention provides a method of processing supercooled fluids to overcome the above difficulties. When processed by the method constituting this invention, the fluid tends to remain stable in the liquid state for extended periods of time, even when the fluids are subjected to temperatures below the freezing temperature of water. Furthermore, the fluids become triggered from the liquid state to the solid crystalline state at a substantially constant temperature, the value of which can be predetermined. The supercooled fluid may constitute sodium thiosulfate pentahydrate.

When supercooled fluid is processed by the method constituting this invention, a suitable material such as ethylene glycol may be added to the supercooled fluid to enhance the stability of the supercooled fluid and to provide for the generation of heat in the supercooled fluid at a desired temperature less than the melting temperature of the supercooled fluid. The mixture of the ethylene glycol and the supercooled fluid is then heated to a relatively high temperature considerably above the melting temperature of the supercooled fluid. With the mixture at the particular temperature, water is added to provide a specific gravity of a particular value and a suitable material such as sodium hydroxide or sodium carbonate is added to provide a particular pH.

The mixture may then be poured into rupturable packages while being maintained at the particular temperature. The mixture is then allowed to cool slowly in the rupturable packages to ambient temperatures and a trigger is added in a separate container after the cooling of the mixture to ambient temperature. The container then holds the package of the supercooled fluid and the trigger in isolated relationship to each other. The trigger may constitute a suitable material such as sodium borate pentahydrate.

In the drawings:

FIG. 1 is a perspective view, partially broken away, of one embodiment of the invention; and FIG. 2 is a sectional view substantially on the line 2—2 of FIG. 1; and FIG. 3 is a schematic view showing apparatus used to provide the method constituting this invention.

In one embodiment of the invention, a pouch or packet 10 contains a supercooled fluid 12. The pouch is provided with a rupturable seal 14 along one edge, the seal being ruptured when subjected to a particular pressure such as results from a manual pounding or a manual squeezing of the pouch. The pouch 10 is disposed in a container 16 which also contains a trigger material 18 for the supercooled fluid. As will be seen, the trigger material 18 is disposed in isolated relationship to the supercooled fluid in the pouch 10.

A number of different materials can be used as the supercooled fluid 12. These materials include sodium sulfate decahydrate, sodium thiosulfate pentahydrate (hypo), sodium hydrogen phosphate, sodium chromate decahydrate, calcium chloride hexahydrate, magnesium chloride with water, magnesium nitrate hexahydrate and urea/ammonium nitrate. The trigger material 18 in the container 16 may be sodium borate.

When the pouch 10 is ruptured, the supercooled fluid 12 in the pouch is mixed with the trigger material 18 and becomes triggered from the liquid state into a solid crystalline state. This causes heat to be liberated at a substantially constant temperature during the time that the supercooled fluid is being converted into the crystalline state. The conversion of the supercooled fluid into the crystalline state occurs over an extended period of time so that the temperature produced at the surface of the container 16 is substantially constant for this extended period of time.

The particular temperature obtained by the triggering of the supercooled fluid to the crystalline state can be controlled by the addition of another material into the supercooled fluid to form a mixture. For example, when ethylene glycol is added to hypo, the temperature produced decreases in accordance with the amount of the ethylene glycol added. When the mixture of the hypo and the ethylene glycol contains approximately ten percent (10%) of the ethylene glycol by weight, the temperature produced from the triggering of the hypo into the crystalline state is approximately 104° F. This constitutes a decrease from a temperature of approximately 116° F. which is produced when the fluid in the pouch 10 is substantially only hypo. A relatively small amount of ethylene glycol such as less than approximately two percent (2%) by weight is also effective in the hypo to limit the size of the crystals produced from the hypo when the supercooled fluid is triggered into the solid state. The amounts of ethylene glycol to approximately two percent (2%) tends to control the size of the crystals produced by triggering the supercooled fluid. The use of ethylene glycol for the above purposes is disclosed in co-pending application Ser. No. 866,695 filed by Gustaf O. Arrhenius on Jan. 3, 1978, and assigned of record to the assignee of record of this application.

In order that the mixture in the pouch 10 is stable under a wide range of conditions and that it will produce a predetermined temperature when triggered, the mixture is processed by the method constituting the invention. As a first step, the mixture is disposed in kettles 20 made from a suitable material such as stainless steel so that the supercooled fluid in the mixture will not become contaminated. The kettles 20 may be electrically heated and may be provided with closed tops to assure that contaminants are not introduced into the kettles while the mixture in the kettles is processed. The kettles are then heated electrically so that the mixture in the kettles reaches a suitable temperature considerably above the melting temperature of the supercooled fluid. For example, the mixture may be heated to a suitable temperature such as approximately 180° F. An agitator 22 may be operated from the time that the melting of the supercooled fluid in crystalline form is initiated. By heating the mixture containing the supercooled fluid to a temperature considerably above the melting temperature of the supercooled fluid and agitating the mixture during the heating operation, the melting of all crystals, even those of minute size, is facilitated. This assures that the supercooled fluid will remain in liquid form even after being cooled since the minutes crystals might otherwise operate to initiate the process of crystallization. Furthermore, by heating the supercooled fluid at a temperature of approximately 180° F., the supercooled fluid tends to become pasteurized and thereby inhibit bacterial growth.

When the temperature of the mixture has reached a value such as approximately 180° F. and the melting of the crystals in the supercooled fluid at substantially that temperature has been completed, water is added at that temperature to adjust the specific gravity to a particular value such as 1.595±0.005. The specific gravity of the mixture is adjusted in this manner to assure that the supercooled fluid will remain in the supercooled state after the fluid has been cooled to ambient temperatures. If insufficient water is added to the mixture to provide the particular value desired for the specific gravity, the supercooled fluid will tend to become self-triggered into the crystalline state, particularly when the supercooled fluid becomes cooled. Furthermore, the insufficiency of water in the mixture causes the supercooled fluid in the mixture to become crystallized at a temperature of approximately 120° F. instead of 118° F. which is normally the melting and crystallizing temperature of hypo.

It has been recently found that minute crystals of the hypo in the dihydrate phase normally exist in hypo which has been supercooled. Such minute crystals tend to serve as nuclei in triggering the supercooled fluid into crystals at times when the triggering is not desired. This causes the supercooled hypo fluid to be unstable when the minute crystals of hypo dihydrate exist in the supercooled hypo.

It has also recently been found that the minute crystals of the hypo dihydrate have a melting temperature of approximately 74° C. (167° F.). In accordance with this invention, a sufficient amount of water is added to the hypo to insure that all of the hypo will be in the α-pentahydrate phase. It is desirable to maintain the hypo in the α-pentahydrate phase since the production of crystals in the α-pentahydrate phase causes five (5) to ten (10) times more heat to be liberated than the production of crystals in any other phase including the dihydrate phase.

As will be appreciated, only a sufficient amount of water is added to insure the maintenance of the hypo in the α-pentahydrate phase. If additional water is added above the amount required, some additional assurance may be provided of maintaining the hypo in the α-pentahydrate phase but the hypo is diluted so that the heat generated by crystallizing a specified amount of fluid is decreased. The hypo is then heated to a temperature of at least 74° C. (165° F.) for a sufficient period of time to melt all of the minute crystals of hypo in the dihydrate phase.

The hypo is then cooled in air to ambient temperatures and the hypo is maintained in a stable state at ambient temperatures until it is desired to generate heat by triggering the hypo in the crystalline phase after such heat has been liberated and utilized. The hypo is converted to the liquid state in the α-pentahydrate phase by heating the crystals to a temperature of at least 74° C. (167° F.) for a specified period of time. No water has to be added if the hypo is maintained in a closed container. In this way, the hypo can be recycled between the liquid state with the α-pentahydrate phase and the crystalline state with the α-pentahydrate phase as many times as desired without the addition of any water.

The pH of the solution is also adjusted to a particular value during the time that the temperature of the mixture is maintained at the particular temperature such as approximately 180° F. For example, the pH of the mixture is adjusted to a value of approximately 8 to 8.5. By adjusting the pH to a value of approximately 8 to 8.5, the hypo is maintained in the solution. For example, unless the pH of the hypo is maintained at the specified value, the hypo may decompose chemically and form a colloidal suspension of sulfur. This colloidal suspension of sulfur is capable of nucleating the hypo at undesired times so that the solution of hypo becomes unstable. Furthermore, a pH of 8 to 8.5 inhibits recrystallization of the fluid after the temperature of the fluid has returned to ambient values. The maintenance of the hypo at a pH of approximately 8 to 8.5 has been obtained by adding controlled amounts of a suitable material such as sodium hydroxide or sodium carbonate to the mixture. The sodium hydroxide may have a concentration of approximately twenty-five percent (25%) with the remainder consituting water. The sodium carbonate may have a similar concentration.

The mixture is then pumped at the elevated temperature of approximately 180° F. through pipes 30 made from a suitable material such as stainless steel to prevent contamination of the mixture. The fluid is then introduced to a storage tank 32 also made from a suitable material such as stainless steel to inhibit the introduction of contaminants into the mixture. The temperature of the storage tank 32 is controlled to maintain the solution at a suitable temperature considerably above the melting temperature of the supercooled fluid. For example, the temperature of the storage tank may be maintained at a suitable temperature of approximately 185° F.±5° F.

The storage tank 32 is disposed above a packaging machine 34 to introduce the mixture into the packaging machine. The packaging machine introduces the fluid into the pouches 10 and fills the pouches with the mixture of the supercooled fluid, water, sodium hydroxide and ethylene glycol and then seals the packages. The fluid passing through the packaging machine into the pouches is maintained at a suitable temperature such as approximately 180° F. to inhibit bacterial growth in the fluid during the filling and sealing of the pouches 10 and to prevent the reformation of minute crystals which subsequently serve as nuclei for producing crystallization of the supercooled fluids at undesirable times.

The pouches 10 are allowed to cool slowly under ambient conditions to room temperature. This cooling process may last for a period as long as four (4) days. One purpose of this long cooling process is to provide ample opportunity to determine integrity of the seals provided on the pouch 10. Another purpose is to prevent the supercooled fluid from forming small nuclei for subsequently producing crystallization of the supercooled fluids at undesirable times. If the pouch 10 is introduced into the container 16 with the triggering material 18 during the time that the mixture is above ambient temperature, there is a tendency for the supercooled fluid 12 to become triggered into the crystallized state. By insuring that the supercooled fluid 12 has been cooled to ambient temperature before the pouch 10 and the trigger material 18 are inserted into the container 16, any tendency for the supercooled fluid to become triggered into a state of crystallization in the presence of the trigger material becomes inhibited.

The material constituting this invention has certain important advantages. It provides a supercooled fluid which produces a substantially constant and predetermined temperature to any temperature desired. Furthermore, the material is quite stable at ambient temperatures even when the ambient temperatures are below 32° F., the freezing point of water. In this way, the supercooled fluid can be shipped through long distances and can be retained in the supercooled state during such long shipments so that it is ready to be used to generate heat at the end of such shipments. The advantages of such material result in part from the methods used to produce such materials.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. A method of producing sodium thiosulphate in only the pentahydrate phase, including the following steps:

heating the aqueous solution of sodium thiosulphate pentahydrate to a temperature of at least 165° F. for a sufficient period of time to melt all of the crystals in the sodium thiosulphate pentahydrate, maintaining the solution alkaline, and adding water to the solution to maintain the specific gravity of the solution at a particular value for inhibiting the self-triggering of the sodium thiosulphate into the crystalline state.

2. A method as set forth in claim 1 wherein the solution is allowed to cool for an extended period to ambient temperatures after being heated.

3. A method set forth in claim 2 wherein the pH is maintained at a value above approximately 8 by adding to the solution an alkali selected from the group consisting of sodium hydroxide and sodium carbonate.

4. The method set forth in claim 2 wherein the particular specific gravity is approximately 1.595.

5. The method set forth in claim 4, including the step of:

disposing the sodium thiosulphate in a container while the sodium thiosulphate is at the elevated temperature of at least 165° F.

6. The method set forth in claim 1 wherein the elevated temperature is approximately 180° F.

7. The method set forth in claim 2 wherein the elevated temperature is approximately 180° F. and water is added to the sodium thiosulphate to maintain the specific gravity at a value of approximately 1.595.

8. A method of producing sodium thiosulphate in only the pentahydrate phase, including the following steps:

adding to the sodium thiosulphate a chemical selected from the group consisting of glycerol and ethylene glycol for lowering the melting point to the solution and for limiting the size of the crystals in the solid state, heating the mixture of the sodium thiosulphate pentahydrate and the chemical to a temperature of at least 165° F. for a sufficient period of time to melt all of the crystals of sodium thiosulphate pentahydrate in the solution, adding water to the mixture to maintain the specific gravity of the mixture at a value of approximately 1.595, and maintaining the solution alkaline.

9. The method set forth in claim 8, including the step of disposing the mixture in a container while the mixture is maintained at substantially the elevated temperature of at least 165° F.

10. The method set forth in claim 8, including the step of
cooling the mixture in air to ambient temperatures.

11. The method set forth in claim 10 wherein the elevated temperature is approximately 180° F.

12. The method set forth in claim 8 wherein an alkali selected from the group consisting of sodium hydroxide and sodium carbonate is added to the mixture to maintain the pH of the solution above a value of approximately 8.

* * * * *